United States Patent [19]

Tom

[11] 4,444,880

[45] Apr. 24, 1984

[54] PERIODATE REMOVAL OF ASCORBATE INTERFERENCE IN DIPSTICKS FOR IMMUNOASSAYS

[75] Inventor: Henry Tom, La Honda, Calif.

[73] Assignee: Syva Company, Palo Alto, Calif.

[21] Appl. No.: 402,452

[22] Filed: Jul. 27, 1982

[51] Int. Cl.³ .................... G01N 33/54; G01N 33/52; G01N 33/58

[52] U.S. Cl. ........................................ 435/7; 422/56; 435/4; 435/28; 435/805; 436/175; 436/176; 436/530; 436/810; 436/825

[58] Field of Search ............. 436/7, 28, 805, 4; 436/530, 825, 810, 175, 176; 422/56

[56] References Cited

U.S. PATENT DOCUMENTS

| 3,856,469 | 12/1974 | Schneider | 436/825 X |
| 4,168,146 | 9/1979 | Grubb | 436/810 X |
| 4,252,783 | 2/1981 | Kam | 436/825 |
| 4,310,626 | 1/1982 | Burkhardt | 435/805 X |
| 4,362,531 | 12/1982 | de Steenwinkel | 436/825 X |

OTHER PUBLICATIONS

Chemical Abstracts I, 90:119481f, (1979).
Chemical Abstracts II, 91:191113a, (1979).
Chemical Abstracts III, 95:93433t, (1981).

Primary Examiner—Sidney Marantz
Attorney, Agent, or Firm—Bertram I. Rowland

[57] ABSTRACT

A solid support "dipstick" immunoassay impregnated with sodium metaperiodate ($NaIO_4$) is described wherein ascorbate interference with an assay having a peroxidase signal producing system is reduced or eliminated.

11 Claims, No Drawings

PERIODATE REMOVAL OF ASCORBATE INTERFERENCE IN DIPSTICKS FOR IMMUNOASSAYS

BACKGROUND OF THE INVENTION

1. Field of the Invention

A "dip-stick" immunoassay provides a simple and rapid technique for measuring the presence and amount of an analyte in a sample solution. The analyte may be present in serum, urine, saliva, etc. and may consist of any of a wide variety of materials, such as drugs, naturally occuring physiological compounds, pollutants, or the like.

Various signal producing techniques are employed for developing a detectable signal related to the presence or amount of an analyte. One desirable system employs horse radish peroxidase to oxidize a dye precursor to a dye. Ascorbate affects this reaction so that the amount of dye which is produced can vary with the amount of ascorbate present in the assay medium.

Since samples, which are assayed are frequently physiological fluids having widely varying amounts of ascorbate, unless the ascorbate interference can be diminished to a satisfactory level, the assay can only provide erratic and uncertain results. It is therefore desirable to find a simple efficient and economic way for reducing ascorbate interference without otherwise interfering with other assay reagents or increasing the complexity of the protocol.

2. Brief Description of the Prior Art

The basic dipstick immunoassay technique is discussed at length in U.S. Pat. No. 4,299,916. A pretreatment of serum prior to an assay of thyroxine is disclosed in U.S. Pat. No. 4,121,975. The addition of soluble iodate to eliminate interference from reducing agents when detecting redox reactions is disclosed in European Pat. No. 76,076D. The use of $HIO_4$ and/or its salts to remove interfering reducing substances is disclosed in Japanese Patent Application No. 81/109,595.

SUMMARY OF THE INVENTION

In an immunoassay employing a bibulous solid support, where the production of a dye by oxidation of a dye precursor with horseradish peroxidase is the means for detecting the presence and/or amount of an analyte, the bibulous support is impregnated with metaperiodate to reduce ascorbate interference to acceptable levels.

DESCRIPTION OF THE SPECIFIC EMBODIMENTS

The subject invention is an improvement in an immunoassay for measuring a wide variety of analytes, where the immunoassay employs a bibulous support and horseradish peroxidase and a dye precursor for production of a detectable signal. In the assay, the enzyme is conjugated to a member of a specific binding pair, either a receptor or a ligand (hereinafter referred to as "mip"), so that the binding of the enzyme to the bibulous support is related to the amount of analyte in the assay medium. By having a substrate which acts as a dye precursor, the amount of dye which binds to the bibulous support is related to the amount of analyte in the media. It is found, however, that ascorbate affects the amount of dye which is produced. Since ascorbate can widely vary in the physiological fluids which are the primary source of samples, in order to have a satisfactory assay, the ascorbate interference must be reduced to an acceptable level. In accordance with this invention, ascorbate interference is reduced to such level by impregnating the bibulous support which is employed with metaperiodate, particularly a water soluble metaperiodate, more particularly an alkali metal metaperiodate.

The amount of metaperiodate which is impregnated into the support may be widely varied so long as it exceeds a particular minimum. Usually the bibulous support will be saturated with a solution at least about 0.01 M periodate, more usually at least about 0.05 M periodate and preferably at least about 0.1 M periodate. Amounts in excess of 0.5 M are usually not required and will normally not be exceeded, the amount generally not exceeding 0.2 M periodate.

A wide variety of bibulous supports may be employed, particularly cellulosic supports, such as paper. The periodate solution will generally contain other additives which become simultaneously impregnated. These other additives serve a variety of purposes, such as stabilization of materials bound to the paper, reduction of nonspecific binding, or other purpose. Various proteins can be used, conveniently serum albumins which will generally be present in from about 0.5 to 5 mg/ml. Desirably, other stabilizers or antioxidants will be used, conveniently sugars, such as sucrose which will generally be present in the solution in from about 5 to 25 weight percent.

The manner in which additional materials, particularly mips and enzymes, are bound to the bibulous support may be varied widely in accordance with conventional techniques. The papers can be activated in a variety of ways, by providing for aldehyde groups, carboxy groups, amino groups, or the like. The particular mode of activation will depend to a substantial degree on the material which is to become bound to the support. In some instances, merely impregnating the suport with the material of interest will suffice without requiring covalent bonding, e.g. proteins such as antibodies.

In the preferred embodiment of the subject invention, enzymes are covalently bound to the bibulous support, which act on a substrate to produce hydrogen peroxide. Particularly, glucose oxidase may be employed.

The paper may be activated with carbodiimide in accordance with conventional techniques, followed by contacting the support with a solution of glucose oxidase. Where other proteinaceous substances are also to be bound to the support, e.g., antibodies, these may also be included in the solution containing the enzyme. Alternatively where small ligands are to be bound to the bibulous support, the ligand will frequently be functionalized so as to be capable of reacting with the bibulous support to form stable covalent bonds.

The various reagents involved with the assay, such as enzymes and mips will be bound to the bibulous support prior to impregnation with periodate. Therefore, the method of binding must be stable to both the periodate impregnation and the assay conditions.

The assay conditions will involve a buffered aqueous medium, pH in the range of about 6–10. Various protocols may be employed, where the dipstick is contacted with the sample and mip-HRP conjugate simultaneously or successively, generally followed by contact with the developer solution containing the dye precursor. The disclosure of U.S. Pat. No. 4,299,916 is incorporated herein by reference as describing the conditions and specific reagents of the assay.

In order to demonstrate the subject invention, a number of bibulous supports were prepared and tested to demonstrate the effectiveness of the subject invention.

Initially, test papers were impregnated with various sample compositions that were tested for their ability to block ascorbate interference. Ten sheets of Whatman No. 1C paper disks were prepared for impregnation with soluble test compositions during incubation in a BSA-sucrose/buffer solution at pH 7.0; control papers containing no test compositions were also prepared. The paper disks were activated to readily immobilize protein as described in U.S. Pat. No. 4,299,916 and, thereafter, they were washed with buffer.

The activated papers were placed into a protein solution for 4 hours to produce a protein immobilized solid support. The protein solution was composed of 250 μg/ml Abm (antibody to morphine) stock 66.6 mg/ml at pH 7; 0.1 M phosphate with 0.2 M NaCl; 2% QS-44 (detergent); 100 μg/ml GO(NH$_2$)$_x$ (glucose oxidase, including amine groups to make it bind to the support more readily) from stock 10 mg/ml. The paper was washed with a buffer and incubated in a BSA-sucrose/buffer and test composition solution for 1.5 hours before lyophilization. The BSA/sucrose was included as a protein preservative.

The test compositions evaluated had to meet a solubility criteria of 0.1 M in pH 7 BSA-sucrose (2 mg/ml-15% w/v). The following test compositions were evaluated.

1. Ammonium persulfate (molecular weight 228), 0.57 g/25 ml;
2. Sodium stannate (molecular weight 266.7), 0.667 g/25 ml;
3. Sodium metaperiodate (molecular weight 214), 0.555 g/25 ml;
4. O-iodoso benzoic acid (molecular weight 264), 0.66 g/25 ml;
5. Potassium dichromate (molecular weight 294), 0.75 g/25 ml;
6. 2-chlorophenylhydrazine (molecular weight 179), 0.45 g/25 ml;
7. Sodium bromate (molecular weight 151), 0.38 g/25 ml;
8. NaOCl (5.25% solution), 3.55 ml; and
9. NaClO$_4$ (4 M solution), 0.65 ml.

The purpose of the evaluation of test compositions was to determine if paper impregnated with the test composition reverses or eliminates ascorbate interference with an assay signal producing system.

The test composition impregnated papers were incubated for one minute in a sample containing a standard phosphate/NaCl buffer and negative morphine, and for seven minutes in a developer consisting of 0.05 M Phosphate, pH 6.5; 50 mM glucose; 2 mg/ml BSA; 400 μg/ml 4-Cl-1-Naphthol; and 300 ng/ml HRP-M (Horse Radish Peroxidase/Morphine Complex).

The results of the test composition evaluation appear in the following table (in Color Difference Units as measured with a Macbeth reflectance spectrophotometer):

| | TEST COMPOSITIONS | | | | | |
|---|---|---|---|---|---|---|
| Normal | Io-date | Stan-nate | Perio-date | O—iodoso benzoic acid | Bromate | Per-chlorate |
| No Ascorbate | | | | | | |
| 18.8 | 19.1 | 10.4 | 17.6 | 16.0 | 15.2 | 18.6 |
| -continued | | | | | | |
| 17.0 | 18.1 | 12.0 | 17.5 | 15.5 | 17.7 | 18.4 |
| Ascorbate 200 mg/dl | | | | | | |
| 5.4 | 16.1 | 5.2 | 15.9 | 8.8 | 3.8 | 5.8 |
| 4.4 | 14.7 | 5.6 | 15.7 | 7.4 | 5.7 | 5.8 |

Only two of the test compositions reversed ascorbate interference with an assay signal producing system to an acceptable level. These are iodate and periodate.

The next test was a comparison of reproducibility with normal paper and with paper impregnated with 300 mM periodate (PI-300) and BSA-sucrose. Periodate impregnation took place during the BSA-sucrose/buffer incubation step. A 3.5 hour protein paper incubation was followed by a 25 minute periodate/BSA-sucrose/buffer incubation before lyophilization. The protein solution consisted of 250 μg/ml Abm, 2% QS-44, 100 μg/ml GO(NH$_2$)$_x$, and a standard buffer of phosphate and NaCl. The paper used was Whatman No. 1C paper disks that were activated as described in U.S. Pat. No. 4,299,916.

A pooled urine sample solution was used containing either positive or negative morphine and either positive or negative ascorbate. The assay consisted of a one minute sample incubation and a 10 minute developer incubation. Postive morphine concentration was 100 ng/ml; positive ascorbate concentration was 200 mg/dl.

Reproducibility with normal paper and with PI-300 paper was essentially identical. Variability increased, but remained at an acceptable level, with the addition of 200 mg/dl ascorbate to the sample solution versus no ascorbate when using a PI-300 dipstick assay.

| Ascorbate* | + | | − | |
|---|---|---|---|---|
| Morphine* | + | − | + | − |
| Mean value | 117 | 161 | 131 | 175 |
| Std. Dev. | 8.86 | 6.89 | 4.87 | 3.78 |
| CV % | 6.91 | 4.27 | 3.72 | 2.11 |
| N | 15 | 14 | 15 | 15 |

*+ - present
− - absent

The results in the presence of ascorbate when the periodate was present were brought into acceptable ranges and the difference average in the presence and absence of ascorbate was the same value for the morphine.

The next test determined the effects of increasing ascorbate concentration on total produced color (ascorbate inhibition) and modulated signal (positive and negative morphine) with 100 mM periodate (PI-100), and 300 mM periodate (PI-300) papers.

The protocol, involved a one minute sample solution incubation and a 10 minute developer incubation. Ascorbate levels were 0, 25, 50, 100, and 200 mg/dl; positive morphine level was 100 ng/ml. The results were as follows (Color Difference Units):

| Morphine | +/− | [ASCORBATE]mg/dl | | | | |
|---|---|---|---|---|---|---|
| | | 0 | 25 | 50 | 100 | 200 |
| PI-100 | − | 17.26 | 17.58 | 16.92 | 16.29 | 14.69 |
| | − | 17.42 | 16.91 | 16.85 | 16.42 | 14.28 |
| | + | 13.35 | 13.26 | 13.28 | 12.69 | 11.31 |

-continued

| Morphine | +/− | [ASCORBATE]mg/dl | | | | |
|---|---|---|---|---|---|---|
| | | 0 | 25 | 50 | 100 | 200 |
| | + | 13.33 | 12.67 | 12.79 | 12.46 | 11.31 |
| PI-300 | − | 17.70 | 17.20 | 16.83 | 16.52 | 15.36 |
| | − | 17.03 | 17.36 | 16.78 | 16.51 | 16.09 |
| | + | 12.43 | 13.31 | 13.11 | 12.52 | 10.99 |
| | + | 12.32 | 12.70 | 13.27 | 12.29 | 12.45 |

The test indicates that ascorbate levels up to 200 mg/dl produce only minor interference with the dipstick assay when a dipstick paper impregnated with periodate is used.

It is evident from the above results that a dip stick immunoassay impregnated with sodium metaperiodate has greatly enhanced reliability and accuracy due to reduced or eliminated ascorbate interference with the assay signal producing system. It is also apparent that the addition of periodate does not interfere with the assay.

In accordance with the subject invention, a simple and effective mode for avoiding ascorbate interference in an assay involving an oxidoreductase enzyme is provided. The use of metaperiodate allows one to impregnate a bibulous support with the reagent. This can be achieved in the presence of proteins bound to the bibulous support, without degradation of the proteins or interfering with their function. The metaperiodate acts while bound to the surface to inhibit ascorbate interference with the enzymatic production of the dye, while having no observable adverse effect on either the dye precursor or the dye. In this way the metaperiodate acts as a selective reagent for removing interference, while in itself does not adversely affect the assay.

Although the foregoing invention has been described in some detail by way of illustration and example for purposes of clarity and understanding, it should be obvious that certain changes and modifications may be practiced within the scope of the appended claims.

What is claimed is:

1. In an immunoassay employing a bibulous support to which is attached a mip and the amount of a mip-peroxidase conjugate which binds to the mip on the support is related to the amount of analyte in a sample, where the peroxidase catalyzes the formation of a dye which binds to said support and ascorbate in said sample interferes with the production of said dye, the improvement which comprises:

impregnating said support with a sufficient amount of periodate to reduce said ascorbate interference to a level which does not interfere with the detection of said analyte.

2. A method according to claim 1, wherein said support impregnated with periodate is further impregnated with a composition comprising a protein and a saccharide in an amount sufficient to stabilize a proteinaceous mip or an enzyme bound to said support.

3. A method according to claim 2, wherein said composition comprises albumin and sucrose.

4. A method according to claim 1, wherein an oxidase capable of catalyzing the formation of hydrogen peroxide is bound to said support.

5. A method according to claims 1 or 4, wherein an antibody is bound to said support.

6. A bibulous support for use in an immunoassay, to which support a mip is attached, wherein the amount of a mip-peroxidase conjugate which binds to the mip on the support is related to the amount of analyte in the sample and wherein the peroxidase catalyzes the formation of a dye which binds to said support and wherein ascorbate in said sample interferes with the production of said dye, said support containing periodate in an amount sufficient to reduce said ascorbate interference to a level which does not interfere with the detection of said analyte.

7. The support of claim 6 further containing an oxidase capable of catalyzing the formation of hydrogen peroxide.

8. The support of claim 6 wherein the mip is an antibody.

9. The support of claim 7 wherein the mip is an antibody.

10. The support of claim 6 further containing an amount of a composition comprising a protein and a saccharide in an amount sufficient to stabilize a proteinaceous mip or an enzyme attached to said support.

11. The support of claim 10 wherein said composition comprises albumin and sucrose.

* * * * *